(12) United States Patent
Takamatsu et al.

(10) Patent No.: US 11,358,928 B2
(45) Date of Patent: Jun. 14, 2022

(54) METHOD FOR PRODUCING PENTAMETHYLENE DIISOCYANATE

(71) Applicant: MITSUI CHEMICALS, INC., Tokyo (JP)

(72) Inventors: Koji Takamatsu, Omuta (JP); Masashi Shimamoto, Tamana (JP); Tomohiro Kano, Yame (JP)

(73) Assignee: MITSUI CHEMICALS, INC., Tokyo (JP)

( * ) Notice: Subject to any disclaimer, the term of this patent is extended or adjusted under 35 U.S.C. 154(b) by 714 days.

(21) Appl. No.: 16/322,740

(22) PCT Filed: Oct. 24, 2017

(86) PCT No.: PCT/JP2017/038234
§ 371 (c)(1),
(2) Date: Feb. 1, 2019

(87) PCT Pub. No.: WO2018/079502
PCT Pub. Date: May 3, 2018

(65) Prior Publication Data
US 2021/0380528 A1    Dec. 9, 2021

(30) Foreign Application Priority Data

Oct. 26, 2016 (JP) .............................. JP2016-209247

(51) Int. Cl.
*C07C 263/10* (2006.01)
*C07C 263/20* (2006.01)

(52) U.S. Cl.
CPC .......... *C07C 263/10* (2013.01); *C07C 263/20* (2013.01)

(58) Field of Classification Search
CPC combination set(s) only.
See application file for complete search history.

(56) References Cited

U.S. PATENT DOCUMENTS

| 3,219,678 | A | * | 11/1965 | Kober ................... C07C 265/14 560/352 |
| 5,552,507 | A | | 9/1996 | Wamprecht |
| 2009/0292100 | A1 | | 11/2009 | Fiene et al. |
| 2010/0249450 | A1 | * | 9/2010 | Maeba ................... C07C 263/20 560/352 |
| 2013/0079486 | A1 | | 3/2013 | Hidesaki |
| 2013/0338330 | A1 | | 12/2013 | Nakagawa |
| 2015/0132808 | A1 | | 5/2015 | Mochizuki |

FOREIGN PATENT DOCUMENTS

| CN | 101495643 A | 7/2009 |
| JP | S58222061 A | 12/1983 |
| JP | 60-54349 A | 3/1985 |
| JP | H05065265 A | 3/1993 |
| JP | H07278088 A | 10/1995 |
| JP | H07309828 A | 11/1995 |
| JP | H11310567 A | 11/1999 |
| JP | H11335344 A | 12/1999 |
| JP | 2010254764 A | 11/2010 |
| JP | 2011132160 A | 7/2011 |
| JP | 2011201863 A | 10/2011 |
| JP | 2012152202 A | 8/2012 |
| JP | 2017031114 A | 2/2017 |
| KR | 10-2010-0101088 A | 9/2010 |
| WO | 2011108473 A1 | 9/2011 |
| WO | 2012121291 A1 | 9/2012 |
| WO | 2013108859 A1 | 7/2013 |

OTHER PUBLICATIONS

Second and Supplementary Notice Informing the Applicant of the Communication of the International Application (to Designated Offices which Apply the 30 Month Time Limit Under Article 22 (1)) (Form PCT/IB/308) dated Feb. 28, 2019, filed in PCT/JP2017/038234.
PCT International Preliminary Reporton Patentability (Form PCT/IB/373) filed in PCT/JP2017/038234, with PCT Notification Concerning Transmittal of International Preliminary Report on Patentability (Form PCT/IB/326) dated May 9, 2019.
PCT International Preliminary Reporton Patentability (Form PCT/IB/373) filed in PCT/JP2017/038234, with PCT Notification of Transmillal of Translation of the International Preliminary Report on Patentability (Form PCT/IB/338) dated May 9, 2019.
International Search Report dated Dec. 5, 2017 filed in PCT/JP2017/038234.

* cited by examiner

Primary Examiner — Brandon J Fetterolf
Assistant Examiner — Blaine G Doletski
(74) Attorney, Agent, or Firm — Rankin, Hill & Clark LLP

(57) ABSTRACT

The method for producing pentamethylene diisocyanate includes a reaction step, in which carbonyl chloride is allowed to react with pentamethylenediamine to produce a reaction mixture containing pentamethylene diisocyanate and a tar component containing a chlorine-containing component; a heating step, in which the reaction mixture is heated; and a purification step, in which the reaction mixture after the heating step is purified to separate the pentamethylene diisocyanate from the tar component, wherein in the heating step, the reaction mixture is heated without removing the tar component from the reaction mixture.

3 Claims, 4 Drawing Sheets

METHOD FOR PRODUCING PENTAMETHYLENE DIISOCYANATE

TECHNICAL FIELD

The present invention relates to a method for producing pentamethylene diisocyanate.

BACKGROUND ART

It has been known that polyisocyanate, i.e., a polyurethane resin material, is conventionally produced by allowing polyamine to react with carbonyl chloride (phosgene).

For example, by allowing hexamethylenediamine as polyamine to react with carbonyl chloride, hexamethylene diisocyanate as polyisocyanate can be produced.

The reaction mixture of hexamethylenediamine and carbonyl chloride contains, in addition to hexamethylene diisocyanate, a by-produced tar component. The tar component is desirably removed, in view of purity of hexamethylene diisocyanate.

Thus, Patent Document 1 has proposed a method for producing hexamethylene diisocyanate, in which nitrogen gas is introduced into a reaction mixture of hexamethylenediamine and carbonyl chloride (phosgene) to remove dissolved phosgene, and then the reaction mixture is subjected to desolvation, further tar removal, and then heating (see Patent Document 1 below).

CITATION LIST

Patent Document

Patent Document 1: Japanese Unexamined Patent Publication No. S58-222061

SUMMARY OF THE INVENTION

Problem to be Solved by the Invention

However, pentamethylene diisocyanate has been gaining attention since the isocyanate group concentration can be improved compared with hexamethylene diisocyanate. Then, the present inventors have examined production of pentamethylene diisocyanate by changing hexamethylenediamine to pentamethylenediamine in the method described in Patent Document 1.

In the examination by the present inventors, it was found that by changing hexamethylenediamine to pentamethylenediamine, carbonyl chloride generated from the tar component separated from the reaction mixture of pentamethylenediamine and carbonyl chloride is significantly large compared with carbonyl chloride generated from the tar component separated from the reaction mixture of hexamethylenediamine and carbonyl chloride, and the separated tar component is low in safety.

The present invention provides a method for producing pentamethylene diisocyanate with which safety regarding the tar component separated from the reaction mixture can be improved.

Means for Solving the Problem

The present invention [1] includes a method for producing pentamethylene diisocyanate including: a reaction step, in which carbonyl chloride is allowed to react with pentamethylenediamine to produce a reaction mixture containing pentamethylene diisocyanate and a tar component containing a chlorine-containing component; a heating step in which the reaction mixture is heated; and a purification step in which the reaction mixture after the heating step is purified to separate the pentamethylene diisocyanate from the tar component, wherein in the heating step, the reaction mixture is heated without removing the tar component from the reaction mixture.

With this method, the reaction mixture is heated without removing the tar component containing a chlorine-containing component from the reaction mixture of carbonyl chloride and pentamethylenediamine.

Therefore, the chlorine-containing component contained in the tar component is decomposed and reduced. Thereafter, the reaction mixture is purified, and pentamethylene diisocyanate is separated from the tar component.

As a result, generation of carbonyl chloride from the separated tar component can be suppressed. In this manner, safety regarding the tar component separated from the reaction mixture can be improved.

The present invention [2] includes the method for producing pentamethylene diisocyanate described in [1] above, wherein the purification step includes a tar-removing step, in which the tar component is separated from the reaction mixture; and a distillation step, in which the reaction mixture after the tar-removing step is subjected to distillation to separate the pentamethylene diisocyanate from the reaction mixture.

With this method, the tar-removing step, in which the tar component is separated from the reaction mixture, is a step different from the distillation step, in which pentamethylene diisocyanate is separated from the reaction mixture, and therefore pentamethylene diisocyanate can be reliably separated from the tar component. Therefore, purity of pentamethylene diisocyanate can be improved.

The present invention [3] includes the method for producing pentamethylene diisocyanate described in [2] above, further including a returning step, in which the distillation residue in the distillation step is returned to the heating step.

However, a heating step may be carried out between the tar-removing step and the distillation step, in view of reduction in the chlorine-containing component. In this case, after the tar component is separated from the reaction mixture in the tar-removing step, the reaction mixture is heated in the heating step, and therefore the tar component is by-produced again. As a result, the distillation residue increases in the distillation step after the heating step.

The distillation residue contains pentamethylene diisocyanate that has not been separated by the distillation. Therefore, as the distillation residue increases, the amount of pentamethylene diisocyanate contained in the distillation residue increases. As a result, when the distillation residue containing a large amount of pentamethylene diisocyanate is returned to the heating step, the pentamethylene diisocyanate yield decreases.

Meanwhile, with the above-described method, after the heating step, the tar-removing step and the distillation step are carried out in sequence. Therefore, the reaction mixture in which the tar component is separated in the tar-removing step is subjected to distillation in the distillation step without being heated. As a result, the distillation residue can be decreased, and also the amount of pentamethylene diisocyanate contained in the distillation residue can be decreased. This allows for improvement in the pentamethylene diisocyanate yield.

The present invention [4] includes the method for producing pentamethylene diisocyanate described in any one of the above-described [1] to [3], wherein the heating temperature in the heating step is more than 160° C.

With this method, the reaction mixture containing the tar component is heated with a heating temperature of more than 160° C. Therefore, the chlorine-containing component contained in the tar component can be reliably reduced.

The present invention [5] includes the method for producing pentamethylene diisocyanate described in any one of the above-described [1] to [4], wherein the residence time in the heating step is 1 hour or more.

With this method, the reaction mixture containing the tar component is heated with a residence time of 1 hour or more. Therefore, the chlorine-containing component contained in the tar component can be reduced more reliably.

The present invention [6] includes the method for producing pentamethylene diisocyanate of any one of the above-described [1] to [5], further including a degassing step after the reaction step and before the heating step, wherein in the degassing step, excessive carbonyl chloride is removed from the reaction mixture.

With this method, excessive carbonyl chloride is removed from the reaction mixture before the heating step. Therefore, carbonyl chloride and chlorine-containing component contained in the reaction mixture can be reduced. As a result, the chlorine-containing component contained in the tar component can be reliably reduced even more.

Effect of the Invention

With the method for producing pentamethylene diisocyanate of the present invention, safety can be improved regarding the tar component separated from the reaction mixture.

DESCRIPTION OF EMBODIMENTS

Figure 1:
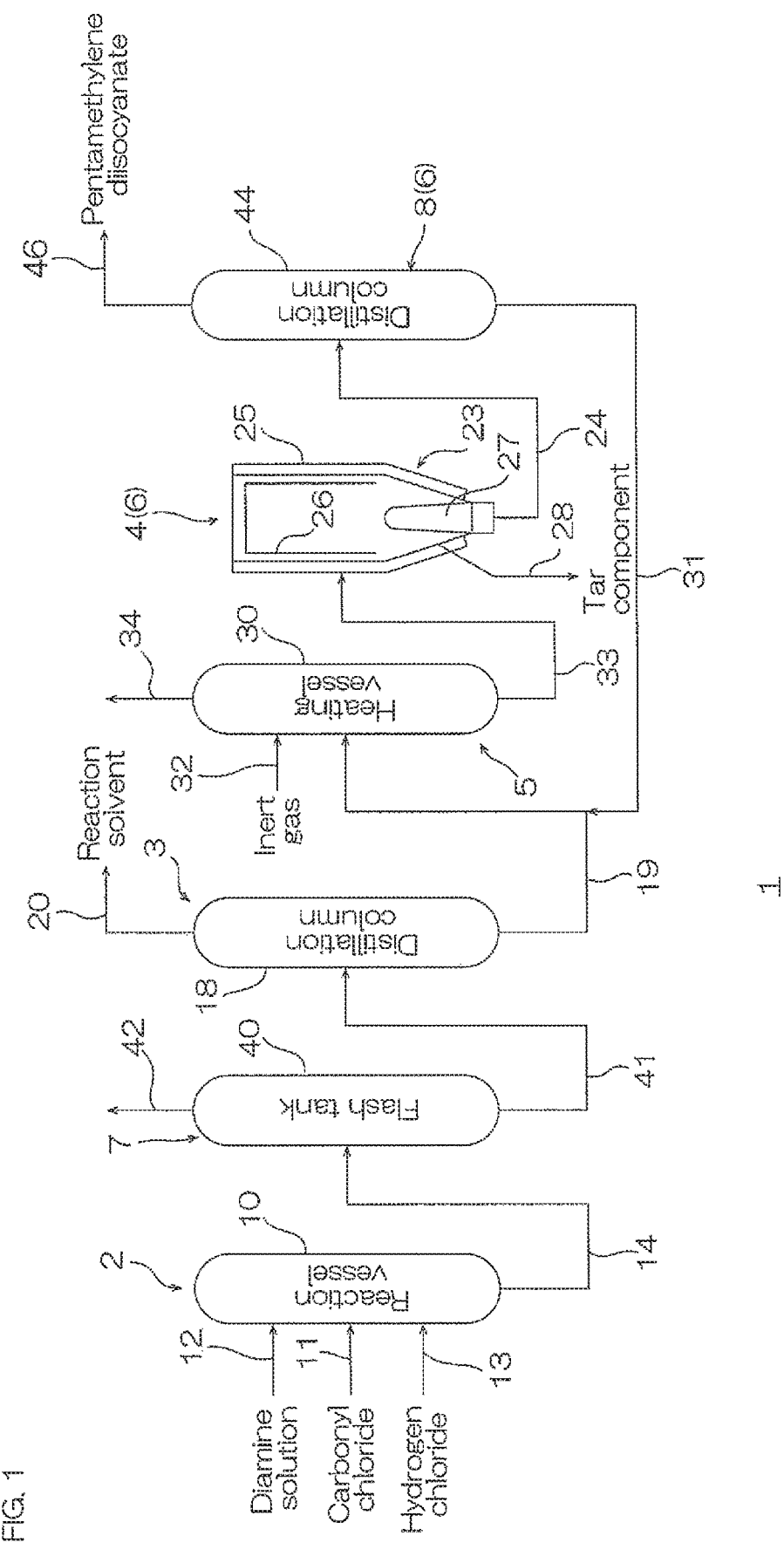
FIG. 1 is a schematic diagram illustrating the configuration of a production system for producing pentamethylene diisocyanate, in which an embodiment of the method for producing pentamethylene diisocyanate of the present invention is carried out.

The method for producing pentamethylene diisocyanate of the present invention includes a reaction step, in which carbonyl chloride is allowed to react with pentamethylenediamine to obtain a reaction mixture, a heating step, in which the reaction mixture is heated, and a purification step, in which the reaction mixture after the heating step is purified.

1. Reaction Step

In the method for producing pentamethylene diisocyanate, first, pentamethylenediamine is allowed to react with carbonyl chloride to produce a reaction mixture.

Examples of the pentamethylenediamine include 1,5-pentamethylenediamine and 1,4-pentamethylenediamine. The pentamethylenediamine can be used singly, or can be used in combination of two or more.

For the pentamethylenediamine, preferably, 1,5-pentamethylenediamine is used. The pentamethylenediamine can be obtained from, for example, commercially available products, or for example, by biochemical methods from decarboxylation of lysine and/or its salts.

In the reaction step, for example, pentamethylenediamine is allowed to react with carbonyl chloride in the presence of a reaction solvent.

The reaction solvent is an organic solvent that is inactive to carbonyl chloride, pentamethylenediamine, and pentamethylene diisocyanate (described later), and for example, aromatic hydrocarbons (for example, toluene, xylene, etc.), halogenated aromatic hydrocarbons (for example, chlorotoluene, chlorobenzene, dichlorobenzene, etc.), esters (for example, butyl acetate, amyl acetate, etc.), ketones (for example, methylisobutylketone, methyl ethyl ketone, etc.) are used. The reaction solvent can be used singly, or can be used in combination of two or more.

Of these reaction solvents, preferably, halogenated aromatic hydrocarbons are used, even more preferably, dichlorobenzene is used.

Pentamethylenediamine can be allowed to react with carbonyl chloride by, a method in which pentamethylenediamine is directly allowed to react with carbonyl chloride (hereinafter referred to as direct method), or a method in which hydrochloride of pentamethylenediamine is suspended in the above-described reaction solvent, and allowed to react with carbonyl chloride (hereinafter referred to as hydrochloride method). Of these methods, preferably, hydrochloride method is used.

By allowing hydrochloride of pentamethylenediamine to react with carbonyl chloride by the hydrochloride method, first, a reaction vessel capable of stirring and having a hydrogen chloride feed line is introduced with a diamine solution, in which pentamethylenediamine is dissolved in a reaction solvent, and then hydrogen chloride is fed to the reaction vessel and the mixture is stirred. In this manner, pentamethylenediamine is mixed with hydrogen chloride, hydrochloride of pentamethylenediamine is produced, and the content of the reaction vessel becomes a slurry (hydrochloride-formation reaction).

The pentamethylenediamine content in the diamine solution is not particularly limited, and for example, it is 3.0 mass % or more, preferably 4.5 mass % or more, and for example, 20 mass % or less, preferably 17 mass % or less.

Relative to one amino group of pentamethylenediamine, for example, 1 time or more in mol, and for example, 10 times or less in mol, preferably 6 times or less in mol of hydrogen chloride is fed.

At this time, the pressure in the reaction vessel is, for example, normal pressure or more, and for example, 1.0 MPa or less, preferably 0.5 MPa or less. In the reaction vessel, the temperature is, for example, 0° C. or more, and for example, less than 180° C., preferably 160° C. or less.

Then, the above-described temperature and pressure are kept in the reaction vessel, and unreacted hydrogen chloride is released outside the reaction system (outside the reaction vessel).

Then, the pressure in the reaction vessel is set to, for example, normal pressure or more, and for example, 1.0 MPa or less, preferably 0.5 MPa or less. The temperature in the reaction vessel is increased to, for example, 80° C. or more and 180° C. or less.

Then, after increasing the temperature, carbonyl chloride is fed, and the carbonyl chloride feeding is continued for, for example, 30 minutes or more and 20 hours or less, allowing reaction (isocyanate-forming reaction, phosgenation).

The progress of the isocyanate-forming reaction can be checked by the amount of hydrogen chloride gas generated, and also by the above-described slurry in the reaction solvent disappearing and the reaction solution (reaction mixture) being transparent and homogenous.

In this manner, carbonyl chloride is allowed to react with pentamethylenediamine hydrochloride, thereby producing pentamethylene diisocyanate as a main component.

The produced pentamethylene diisocyanate is in correspondence to the above-described pentamethylenediamine used as a material component. To be more specific, examples of the produced pentamethylene diisocyanate include 1,5-pentamethylene diisocyanate and 1,4-pentamethylene diisocyanate. For example, when 1,5-pentamethylenediamine is used, 1,5-pentamethylene diisocyanate is produced.

In the above-described manner, a reaction mixture (reaction solution) is produced.

This embodiment preferably further includes, after the reaction step, and before the heating step, a degassing step.

In the degassing step, from the reaction mixture (reaction solution), gasses such as excessive carbonyl chloride in the reaction step and by-produced hydrogen chloride are removed.

The gas can be removed by, a method in which inert gas is fed to aerate, or a method in which the above-described gas is separated from the reaction mixture (reaction solution) by a known flash tank.

To remove the gas from the reaction mixture (reaction solution) by feeding inert gas for aeration, for example, to the reaction mixture of 80 to 220° C., preferably 100 to 170° C., inert gas is fed at a feeding speed of, for example, 0.01 to 0.5/min, preferably 0.02 to 0.2/min per unit volume.

Examples of the inert gas include carbon dioxide, nitrogen, argon, and helium, and preferably, nitrogen is used. The inert gas can be used singly, or can be used in combination of two or more.

To separate the gas from the reaction mixture (reaction solution) by a flash tank, for example, the reaction mixture (reaction solution) containing the gas is introduced into a flash tank and the pressure is abruptly decreased. In this manner, gas is separated from a liquid component (for example, pentamethylene diisocyanate, reaction solvent, etc.).

In the above-described manner, gasses such as excessive carbonyl chloride and by-produced hydrogen chloride are removed from the reaction mixture.

This embodiment further includes, preferably, after the reaction step and before the heating step, a desolvating step. The desolvating step is carried out, even more preferably, after the degassing step.

In the desolvating step, the reaction solvent is removed from the reaction mixture.

To remove the reaction solvent in the desolvating step, for example, the reaction solvent is distilled off from the reaction mixture by a known distillation column.

In the distillation column, the column bottom temperature is, for example, 80° C. or more, preferably 90° C. or more, and for example, 16° C. or less, preferably 150° C. or less. In the distillation column, the column top temperature is, for example, 60° C. or more, preferably 70° C. or more, and for example, 100° C. or less, preferably 90° C. or less. In the distillation column, the pressure is, for example, 1 kPa or more, preferably 2 kPa or more, and for example, 10 kPa or less, preferably 5 kPa or less.

The reaction solvent is removed from the reaction mixture in this manner.

The reaction mixture contains pentamethylene diisocyanate and a tar component.

The tar component is a polyisocyanate residue by-produced in the reaction step. The tar component contains a high molecular weight polyisocyanate and a chlorine-containing component. That is, the reaction mixture contains a chlorine-containing component.

Examples of the high molecular weight polyisocyanate include a pentamethylene diisocyanate multimer (for example, polyisocyanate trimer or a multimer with three or more molecules, etc.), carbodiimide, uretdione, and uretonimine. The tar component can contain a high molecular weight polyisocyanate singly, or in combination of two or more.

The chlorine-containing component is an organic chlorine compound by-produced in the reaction step, and is a compound that produces hydrogen chloride by hydrolysis (hydrolysable chlorine).

The chlorine-containing component concentration in the reaction mixture after both the degassing step and desolvating step is, for example, 2000 ppm or more, preferably 2500 ppm or more, more preferably more than 5000 ppm, particularly preferably more than 10000 ppm, and for example, 20000 ppm or less, preferably 15000 ppm or less. The chlorine-containing component concentration is measured in accordance with "determination of hydrolysable chlorine" described in JIS K-1603-3 (2007).

Examples of the chlorine-containing component include, for example, a coloring component, and a carbonyl chloride-generating component (hereinafter referred to as COC-generating component). The tar component can contain a chlorine-containing component singly, or in combination of two or more.

The coloring component is a compound that causes coloring of polyurethane resin. The coloring component includes chloro-hydroxypyridine-carbamoylchloride, piperidine-carbamoylchloride, dichloroimine, and carbodiimide.

The COC-generating component is a compound that causes carbonyl chloride generation. It is assumed that examples of the COC-generating component include a carbonyl chloride adduct shown in Chemical Formula 1 below. The carbonyl chloride adduct is a compound in which carbodiimide is added with carbonyl chloride, and it is assumed that carbonyl chloride is generated by the equilibrium reaction shown in Chemical Formula 1 below.

Formula (1)

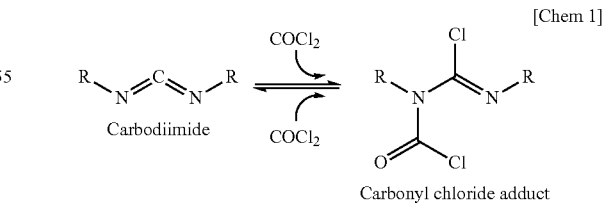

Carbonyl chloride adduct

The reaction mixture of pentamethylenediamine and carbonyl chloride (after both the degassing step and desolvating step) has a high chlorine-containing component concentration in the reaction mixture compared with a reaction mixture of a different type of aliphatic polyamine (for example, hexamethylenediamine) and carbonyl chloride.

For example, a reaction mixture of hexamethylenediamine and carbonyl chloride has a chlorine-containing component concentration of, for example, 10000 ppm or less, preferably 5000 ppm or less.

2. Heating Step

Then, the reaction mixture is heated without removing the tar component from the reaction mixture.

To be specific, the reaction mixture containing the tar component is heated while introducing, as necessary, an inert gas.

In the heating step, to heat while introducing an inert gas to the reaction mixture, for example, first, the reaction mixture is introduced into a heating vessel, and then the inert gas is introduced (fed) into the heating vessel.

The heating vessel is not limited, as long as the vessel is resistant to the heating temperature (described later).

Examples of the inert gas include the above-described inert gas, and preferably, nitrogen is used. The inert gas can be used singly, or can be used in combination of two or more. The inert gas is fed at a speed of, per unit volume of heated liquid (reaction mixture), for example, 0.001/min or more, preferably 0.005/min or more, and for example, 0.2/min or less, preferably 0.1/min or less.

Then, while introducing the inert gas to the reaction mixture continuously, heating is carried out with, as necessary stirring. In this manner, a portion of the reaction mixture is volatilized in the heating vessel, and the reaction mixture is heated.

The heating temperature is, for example, 140° C. or more, preferably more than 150° C., more preferably more than 160° C., and for example, 260° C. or less, preferably 245° C. or less, more preferably 240° C. or less, particularly preferably 220° C. or less.

When the heating temperature is the above-described lower limit or more, the chlorine-containing component in the tar component can be reliably reduced, and when the heating temperature is the above-described upper limit or less, polymerization of pentamethylene diisocyanate in the reaction mixture (polyisocyanate polymerization loss) can be suppressed.

The heating time (residence time) is, for example, 0.1 hours or more, preferably 0.5 hours or more, more preferably 1 hour or more, and for example, 12 hours or less, preferably 10 hours or less, more preferably 8 hours or less, particularly preferably 6 hours or less.

When the heating time is the above-described lower limit or more, the chlorine-containing component in the tar component can be reliably reduced, and when the heating time is the above-described upper limit or less, polymerization of pentamethylene diisocyanate in the reaction mixture (polyisocyanate polymerization loss) can be suppressed.

The pressure in the heating step is, for example, 1 kPa or more, preferably 10 kPa or more, and for example, 1000 kPa or less, preferably 500 kPa or less, even more preferably, normal pressure.

In this manner, the chlorine-containing component (particularly, COC-generating component) contained in the tar component (reaction mixture) is decomposed by heating. Then, the chlorine substance (carbonyl chloride, etc.) derived from the chlorine-containing component is removed as a gas component from the reaction mixture.

To be more specific, the carbonyl chloride adduct as the COC-generating component is efficiently decomposed by being heated to the heating temperature, which allows the equilibrium reaction shown in Chemical Formula 1 above to be more on the carbodiimide side. Then, the chlorine substance (carbonyl chloride, etc.) derived from the chlorine-containing component is removed from the tar component (reaction mixture) as the gas component. Therefore, the COC-generating component (for example, carbonyl chloride adduct, etc.) contained in the tar component (reaction mixture) is reduced.

The coloring component is decomposed by heating, or converted to a high molecular weight substance that is easily separable from pentamethylene diisocyanate in the purification step.

In the following, the reaction mixture after the heating step is called a heated mass.

The chlorine-containing component concentration of the heated mass is, for example, 100 ppm or more, preferably 200 ppm or more, and for example, 5000 ppm or less, preferably 4000 ppm or less.

When the chlorine-containing component concentration of the heated mass is the above-described upper limit or less, the chlorine-containing component concentration of the separated tar component described later can be reliably reduced, and generation of carbonyl chloride from the separated tar component can be reliably suppressed.

The chlorine-containing component concentration in the heated mass is, setting the chlorine-containing component concentration in the preheating reaction mixture to 100 mass %, for example, 1 mass % or more, preferably 2 mass % or more, and for example, 50 mass % or less, preferably 40 mass % or less.

In the heating step, a catalyst or an additive can be added to the reaction mixture.

Examples of the additive include metals such as iron, copper, and zinc. These metals may be used singly, or in a combination of two or more. For the metal, preferably, copper is used.

The amount of the metal added is not particularly limited, and is suitably set in accordance with purpose and use. For example, relative to 100 parts by mass of pentamethylene diisocyanate, for example, 0.01 mass % or more, preferably 0.1 mass % or more, more preferably 0.15 mass % or more, and for example, 0.50 mass % or less, preferably 0.40 mass % or less, more preferably 0.30 mass % or less of the metal is added.

The metal can be added at any time, without particular limitation. For example, the metal can be added before heating, during heating, or both.

When a metal is added in the heating step, reaction between the metal and the chlorine atom of the chlorine-containing component may cause production of metal chloride (for example, copper chloride, iron chloride, zinc chloride).

The metal chloride content relative to 100 mass % of the heated mass is, for example, 0.015 mass % or more, preferably 0.15 mass % or more, and for example, 1.0 mass % or less, preferably 0.7 mass % or less.

3. Purification Step

Then, the reaction mixture (heated mass) after the heating step is purified, to separate pentamethylene diisocyanate from the tar component.

In this embodiment, after separating the tar component from the heated mass (tar-removing step), the reaction mixture from which the tar component is separated is distilled to separate pentamethylene diisocyanate from the reaction mixture (distillation step). That is, in this embodiment, the purification step includes a tar-removing step and a distillation step.

3-1. Tar-Removing Step

In the tar-removing step, the tar component is removed from the heated mass by, for example, a known thin film evaporator.

The temperature in the tar-removing step is, for example, 100'C or more, preferably 110° OC or more, and for example, 150° C. or less, preferably 140° C. or less. The pressure in the tar-removing step is, for example, 2.6 kPa or less, preferably 1.3 kPa or less.

In this manner, a large portion of the tar component is separated from the heated mass. The tar component separated from the heated mass is called a separated tar component in the following. The heated mass (reaction mixture) after the tar removal is called a tar-removed mass.

Relative to 100 mass % of the heated mass fed to the tar-removing step, the separated tar component is separated by, for example, 5 mass % or more, preferably 10 mass % or more, and for example, 30 mass % or less, preferably 20 mass % or less.

Generation of carbonyl chloride is suppressed with the separated tar component, and highly safe.

A portion of the tar component remains in the tar-removed mass. Therefore, the tar-removed mass contains pentamethylene diisocyanate and remained tar component.

The remained tar component relative to 100 mass % of the tar-removed mass is, for example, 0.01 mass % or more, and for example, 1 mass % or less, preferably 0.1 mass % or less.

The pentamethylene diisocyanate content relative to 100 mass % of the tar-removed mass is, for example, 90 mass % or more, preferably 95 mass % or more, and for example, 99 mass % or less.

3-2. Distillation Step

Then, the reaction mixture (tar-removed mass) after the tar-removing step is subjected to distillation to separate pentamethylene diisocyanate from the reaction mixture (tar-removed mass).

The distillation temperature is, for example, 90° C. or more, preferably 100° C. or more, and for example, 160° C. or less, preferably 150° C. or less. The distillation pressure is, for example, 1.0 kPa or more, preferably 2.0 kPa or more, and for example, 4.0 kPa or less, preferably 3.0 kPa or less.

The distillation time (residence time) is, for example, 0.1 hours or more, preferably 0.5 hours or more, more preferably 1 hour or more, and for example, 12 hours or less, preferably less than 10 hours, more preferably 8 hours or less.

In the above-described manner, the tar-removed mass is separated into a highly pure pentamethylene diisocyanate (purified-pentamethylene diisocyanate) and a distillation residue.

The purified-pentamethylene diisocyanate has a purity of, for example, 95 mass % or more, preferably 98 mass % or more, and for example, 100 mass % or less, preferably 99.999 mass % or less.

The purified-pentamethylene diisocyanate is a composition containing pentamethylene diisocyanate and a small amount of chlorine-containing component.

The purified-pentamethylene diisocyanate has a chlorine-containing component concentration of, for example, 5 ppm or more, preferably 10 ppm or more, and for example, 150 ppm or less, preferably 100 ppm or less, more preferably 90 ppm or less.

The distillation residue is a tar-removed mass from which the purified-pentamethylene diisocyanate is separated. The distillation residue relative to 100 parts by mass of the purified-pentamethylene diisocyanate is, for example, 1 part by mass or more, preferably 5 parts by mass or more, and for example, 30 parts by mass or less, preferably 20 parts by mass or less.

When the ratio of the distillation residue relative to the purified-pentamethylene diisocyanate is the above-described lower limit or more, purity of the purified-pentamethylene diisocyanate can be improved, and also distillation residue can be reliably returned to the heating step in the returning step described later. When the ratio of the distillation residue relative to the purified-pentamethylene diisocyanate is the above-described upper limit or less, production efficiency (yield) of the purified-pentamethylene diisocyanate can be improved.

The distillation residue contains pentamethylene diisocyanate and a tar component.

The distillation residue has a pentamethylene diisocyanate concentration of, relative to 100 mass % of the distillation residue, for example, 40 mass % or more, preferably 50 mass % or more, and for example, 98 mass % or less, preferably 95 mass % or less.

The tar component concentration in the distillation residue is, relative to 100 mass % of the distillation residue, for example, 2 mass % or more, preferably 5 mass % or more, and for example, 60 mass % or less, preferably 50 mass % or less.

3-3. Returning Step

In this embodiment, the distillation residue in the distillation step is returned to the heating step. That is, in this embodiment, the method for producing pentamethylene diisocyanate further includes a returning step. To be more specific, the distillation residue is introduced (added) to the reaction mixture before heating, and returned to the heating step.

By adding the distillation residue to the reaction mixture before heating, in the heating step, a high molecular weight substance formation of the chlorine-containing component (particularly, coloring component) can be promoted, and the chlorine-containing component in the reaction mixture can be efficiently converted to a high molecular weight substance. Therefore, the chlorine-containing component remaining in the purified-pentamethylene diisocyanate can be suppressed.

The distillation residue can be added in an amount of, relative to 100 parts by mass of the reaction mixture before adding the distillation residue, for example, 0.5 parts by mass or more, preferably 1 part by mass or more, more preferably 5 parts by mass or more, and for example, 50 parts by mass or less, preferably 40 parts by mass or less, more preferably 30 parts by mass or less.

4. Plant

As shown in FIG. 1, the method for producing pentamethylene diisocyanate is continuously carried out industrially by, for example, a plant 1.

The plant 1 is a production system for producing pentamethylene diisocyanate, in which pentamethylene diisocyanate is produced in the above-described method. The plant 1 includes a reaction unit 2, a degassing unit 7, a desolvating unit 3, a heating unit 5, and a purifying unit 6.

The reaction unit 2 is configured to carry out a reaction step. The reaction unit 2 includes a reaction vessel 10, a hydrogen chloride feed line 13, a carbonyl chloride feed line 11, an amine feed line 12, and a transport line 14.

The reaction vessel 10 is a reaction tank for allowing hydrochloride of pentamethylenediamine to react with carbonyl chloride. The reaction vessel 10 is composed of, for example, a heat-resistant and pressure-resistant vessel that is capable of temperature and pressure adjustment.

The hydrogen chloride feed line 13 is piping for feeding hydrogen chloride to the reaction vessel 10. The downstream end of the hydrogen chloride feed line 13 is connected to the reaction vessel 10. The upstream end of the hydrogen chloride feed line 13 is, although not shown, connected to a tank in which hydrogen chloride is stored.

The carbonyl chloride feed line 11 is piping for feeding carbonyl chloride to the reaction vessel 10. The downstream end of the carbonyl chloride feed line 11 is connected to the reaction vessel 10. The upstream end of the carbonyl chloride feed line 11 is connected to, although not shown, a tank in which carbonyl chloride is stored.

The amine feed line 12 is piping for feeding pentamethylenediamine to the reaction vessel 10. The downstream end of the amine feed line 12 is connected to the reaction vessel 10. The upstream end of the amine feed line 12 is connected to, although not shown, a tank in which a diamine solution, in which pentamethylenediamine is dissolved, is stored.

The transport line 14 is piping for transporting the reaction mixture produced in the reaction vessel 10 to the degassing unit 7. The upstream end of the transport line 14 is connected to a lower end (bottom portion) of the reaction vessel 10. The downstream end of the transport line 14 is connected to a generally center in up-down direction of a flash tank 40 (described later).

The reaction unit 2 can include, although not shown, as necessary, a stirrer for stirring inside the reaction vessel 10.

The degassing unit 7 is configured to carry out the degassing step, and includes a flash tank 40, a flow-line 41, and a discharge line 42.

The flash tank 40 is a known flash tank, and for example, the flash tank described in Japanese Unexamined Patent Publication No. 2009-119346 is used.

The flow-line 41 is piping for transporting the reaction mixture from which gas is removed to the desolvating unit 3. The upstream end of the flow-line 41 is connected to a column bottom portion of the flash tank 40. The downstream end of the flow-line 41 is connected to a generally center in up-down direction of the distillation column 18 (described later).

The discharge line 42 is piping for discharging gas separated from the reaction mixture by the flash tank 40. The upstream end of the discharge line 42 is connected to a column top portion of the flash tank 40.

The desolvating unit 3 is configured to carry out the desolvating step. The desolvating unit 3 includes a distillation column 18, a bottoms line 19, and a distillation line 20.

The distillation column 18 is composed of, for example, a known distillation column capable of temperature and pressure adjustment, and preferably, is a continuous distillation column.

The bottoms line 19 is piping for transporting the reaction mixture from which the bottoms from the distillation column 18, that is, the reaction solvent, is removed, to the heating unit 5. The upstream end of the bottoms line 19 is connected to the column bottom portion of the distillation column 18. The downstream end of the bottoms line 19 is connected to a generally center in up-down direction of the heating vessel 30 (described later).

The distillation line 20 is piping for distilling off the distillate from the distillation column 18, that is, the reaction solvent. The upstream end of the distillation line 20 is connected to the column top portion of the distillation column 18. The downstream end of the distillation line 20 is, although not shown, connected to a solvent tank that collects the solvent, or to the reaction vessel 10, which allows for reuse of the reaction solvent.

The heating unit 5 is configured to carry out the heating step, and includes a heating vessel 30, a gas feed line 32, a heated mass transport line 33, and a discharge line 34.

The heating vessel 30 is composed of, for example, a heat-resistant and pressure-resistant vessel capable of temperature and pressure adjustment and including a horizontal blades mixer.

The gas feed line 32 is piping for feeding the above-described inert gas to the heating vessel 30. The downstream end of the gas feed line 32 is connected to the heating vessel 30. The upstream end of the gas feed line 32 is connected to, although not shown, a gas tank in which inert gas is stored.

The heated mass transport line 33 is piping for transporting the reaction mixture (heated mass) heated in the heating vessel 30 to the purifying unit 6. The upstream end of the heated mass transport line 33 is connected to the lower end portion (bottom portion) of the heating vessel 30. The downstream end of the heated mass transport line 33 is connected to a casing 25 (described later) of the thin film evaporator 23 (described later).

The discharge line 34 is piping for discharging the inert gas fed by the gas feed line 32 from the heating vessel 30. The upstream end of the discharge line 34 is connected to the upper end (top portion) of the heating vessel 30.

The purifying unit 6 is configured to carry out the purification step, and includes a tar removal unit 4, a distillation unit 8, and a returning line 31.

The tar removal unit 4 is configured to carry out the tar-removing step. The tar removal unit 4 includes a thin film evaporator 23, a first discharge line 24, and a second discharge line 28.

The thin film evaporator 23 is a known thin film evaporator, and includes a casing 25, a wiper 26, and an internal condenser 27.

The casing 25 is provided with a jacket for heating inside the casing 25, and a suction pipe (not shown) for reducing the pressure inside the casing 25.

The wiper 26 is disposed inside the casing 25. The wiper 26 is disposed to be slightly spaced apart from the inner periphery of the casing 25. The wiper 26 is rotatable by a motor, which is not shown.

The internal condenser 27 is composed of, for example, a heat exchanger, in which a refrigerant is circulated. The internal condenser 27 is provided, inside the casing 25, at the bottom wall of the casing 25.

The first discharge line 24 is piping for transporting the reaction mixture (tar-removed mass) from which the tar component is removed from the casing 25 to the distillation unit 8. The upstream end of the first discharge line 24 is connected to the internal condenser 27. The downstream end of the first discharge line 24 is connected to a generally center in up-down direction of the distillation column 44 (described later).

The second discharge line 28 is piping for taking out the tar component from the casing 25. The upstream end of the second discharge line 28 is connected to a lower side portion of the casing 25. The downstream end of the second discharge line 28 is connected to a tank for storing the tar component, although not shown.

The distillation unit 8 is configured to carry out the distillation step. The distillation unit 8 includes a distillation column 44, a bottoms line (returning line 31), and a distillation line 46.

The distillation column 44 is composed of, for example, a known distillation column capable of temperature and pressure adjustment, and preferably, is a continuous distillation column.

The returning line 31 is piping for returning the distillation residue to the heating unit 5. The upstream end of the returning line 31 is connected to the column bottom portion of the distillation column 44. The downstream end of the returning line 31 is connected to a portion in the flow direction of the bottoms line 19.

The distillation line 46 is piping for discharging the distillate from the distillation column 44, that is, purified-pentamethylene diisocyanate. The upstream end of the distillation line 46 is connected to the column top portion of the distillation column 44. The downstream end of the distillation line 46 is connected to a tank for storing purified-pentamethylene diisocyanate.

Next, description is given below of operation of the plant 1.

In plant 1, first, the above-described diamine solution is fed to the reaction vessel 10 continuously through the amine feed line 12. Also, hydrogen chloride is continuously fed to the reaction vessel 10 through the hydrogen chloride feed line 13 at the above-described feeding ratio.

In this manner, pentamethylenediamine is mixed with hydrogen chloride to produce hydrochloride of pentamethylenediamine.

Then, carbonyl chloride is continuously fed to the reaction vessel 10 through the carbonyl chloride feed line 11 under the above-described conditions for the reaction step.

In this manner, carbonyl chloride is allowed to react with pentamethylenediamine hydrochloride, to produce pentamethylene diisocyanate as a main component (reaction step). Also, the tar component containing a chlorine-containing component is by-produced.

In the above-described manner, a reaction mixture containing the pentamethylene diisocyanate, tar component, and reaction solvent is produced.

Thereafter, the reaction mixture is introduced into the flash tank 40 through the transport line 14. Then, the reaction mixture is separated into gases such as excessive carbonyl chloride and hydrogen chloride, and a liquid component such as the pentamethylene diisocyanate and reaction solvent (degassing step).

Then, the gas is discharged from the flash tank 40 through the discharge line 42, and the reaction mixture from which the gas was removed is discharged from the flash tank 40 through the flow-line 41, and then transported to the distillation column 18.

Then, the reaction mixture is distilled in the distillation column 18 under the above-described conditions for the desolvating step (desolvating step).

Then, the reaction solvent is distilled off from the distillation column 18 by the distillation line 20. The distilled off reaction solvent is reused, as necessary.

Meanwhile, the reaction mixture from which the reaction solvent is distilled off is transported to the heating vessel 30 from the distillation column 18 as the bottoms line 19 of the distillation column 18 through the bottoms line 19. At this time, the distillation residue returned by the returning line 31 is added at the above-described ratio to the reaction mixture in the bottoms line 19.

To the heating vessel 30, inert gas is fed at the above-described feeding speed through the gas feed line 32. The reaction mixture fed to the heating vessel 30 is heated under the above-described conditions for the heating step without removing the tar component in the heating vessel 30 while introducing the inert gas (heating step).

In this manner, the chlorine-containing component contained in the tar component (reaction mixture) is decomposed by heating. Then, the chlorine substance derived from the chlorine-containing component is discharged from the heating vessel 30 through the discharge line 34 along with the inert gas.

Meanwhile, the reaction mixture (heated mass) after the heating step is transported from the heating vessel 30 to the casing 25 through the heated mass transport line 33.

Then, the heated mass is formed into a liquid film under the above-described conditions for the tar-removing step in the gap between the wiper 26 and the inner periphery of the casing 25.

At this time, the most portion of the tar component is condensed without being evaporated from the liquid film, and is discharged from the second discharge line 28. In this manner, the most portion of the tar component is removed from the heated mass (tar-removing step).

Meanwhile, the heated mass (tar-removed mass) after the tar removal is evaporated by heating, concentrated in the internal condenser 27, and discharged from the first discharge line 24.

Thereafter, the tar-removed mass is transported to the distillation column 44 through the first discharge line 24.

Then, the tar-removed mass is distilled in the distillation column 44 under the above-described conditions for the distillation step (distillation step).

Then, the purified-pentamethylene diisocyanate is distilled from the distillation line 46. The tank bottom (distillation residue) in the distillation column 44 is transported to the bottoms line 19 through the returning line 31.

Pentamethylene diisocyanate (purified-pentamethylene diisocyanate) is continuously produced in the above-described manner.

5. Operations and Effects

With the method for producing pentamethylene diisocyanate, the reaction mixture is heated without removing the tar component containing a chlorine-containing component from the reaction mixture of carbonyl chloride and pentamethylenediamine.

Therefore, the chlorine-containing component contained in the tar component is decomposed and reduced. Thereafter, the reaction mixture is purified, and pentamethylene diisocyanate is separated from the tar component.

As a result, generation of carbonyl chloride from the separated tar component (separated tar component) can be suppressed. In this manner, safety of the separated tar component can be improved.

In this embodiment, after separating the tar component from the reaction mixture, pentamethylene diisocyanate is separated from the reaction mixture (tar-removed mass) by distillation. Therefore, pentamethylene diisocyanate can be reliably separated from the tar component. As a result, purity of pentamethylene diisocyanate can be improved.

In this embodiment, the tar-removed mass is distilled in the distillation step. As a result, the distillation residue can be reduced, and also the amount of the pentamethylene diisocyanate contained in the distillation residue can be reduced. Therefore, the pentamethylene diisocyanate yield can be improved.

In this embodiment, in the heating step, the reaction mixture containing the tar component is heated to a heating temperature preferably more than 160° C. Therefore, the chlorine-containing component can be reliably reduced.

In this embodiment, in the heating step, the reaction mixture containing the tar component is retained for preferably 1 hour or more. Therefore, the chlorine-containing component can be reliably reduced even more.

In this embodiment, before the heating step, excessive carbonyl chloride is removed from the reaction mixture. Therefore, the chlorine-containing component contained in the separated tar component can be reduced reliably even more.

6. Modified Example

In the above-described embodiment, the purification step includes the tar-removing step and the distillation step, but the present invention is not limited to this. The purification step may include only the distillation step.

The above-described embodiment includes the degassing step and the desolvating step, but the present invention is not limited to this. The method for producing pentamethylene diisocyanate does not have to include the degassing step and the desolvating step.

The above-described embodiment includes the returning step, but the present invention is not limited to this. The method for producing pentamethylene diisocyanate does not have to include the returning step.

In the above-described embodiment, the distillation residue is introduced into the preheating reaction mixture in the returning step, and returned to the heating step, but the present invention is not limited to this. In the returning step, the distillation residue may be introduced into the reaction mixture during heating in the heating step.

In the above-described embodiment, in the heating step, the reaction mixture is heated while introducing inert gas, but it is not limited thereto, and the reaction mixture can be heated without introducing inert gas.

EXAMPLES

The present invention is further described in detail based on EXAMPLES below. However, the present invention is not limited to Examples. The specific numerical values in blending ratio (content ratio), property value, and parameter used in the following description can be replaced with upper limit values (numerical values defined with "or less" or "below") or lower limit values (numerical values defined with "or more" or "above") of corresponding numerical values in blending ratio (content ratio), property value, and parameter described in the above-described "DESCRIPTION OF EMBODIMENTS". The "parts" and "%" are based on mass unless otherwise specified.

The measurement methods for the physical properties are described below.

<Chlorine-Containing Component Concentration of Reaction Mixture (Unit: ppm)>

The chlorine-containing component concentration is measured in accordance with Determination of Hydrolysable Chlorine of JIS K-1603-3 (2007).

Example 1

(1) Reaction Step

A pressure reaction vessel equipped with a jacket, electromagnetic induction stirrer, automatic pressure regulating valve, thermometer, nitrogen inlet line, hydrogen chloride inlet line, carbonyl chloride inlet line, condenser, and a material feed pump was charged with a diamine solution in which 380 parts by mass of 1,5-pentamethylenediamine (PDA) was dissolved in 5000 parts by mass of o-dichlorobenzene. Then, stirring was started, vapor was allowed to pass through the reactor jacket, and the internal temperature was kept at about 130° C. Then, 400 parts by mass of hydrogen chloride was added from the hydrogen chloride inlet line, and hydrochloride formation was started at 130° C. under normal pressure. After the completion of the feed, a light-brown white slurry was formed in the pressurized reactor.

Then, the temperature of the liquid inside the reactor was gradually increased to 160° C., and while adding 1350 parts by mass of carbonyl chloride, isocyanate-formation was carried out at a pressure of 0.25 MPa, and a reaction temperature of 160° C. for 6 hours. In the process of the reaction, the liquid inside the pressure reaction vessel turned a light-brown clear solution.

After the completion of the isocyanate-formation, nitrogen gas was allowed to pass through at 100 L/hour at 160° C., and excessive carbonyl chloride and by-produced hydrogen chloride were removed (degassing step). Thereafter, from the reaction solution after the degassing step, o-dichlorobenzene was distilled off at 100° C. under reduced pressure (desolvating step).

In the above-described manner, the reaction mixture was obtained. The reaction mixture contained 1,5-pentamethylene diisocyanate (PDI) and a tar component.

(2) Heating Step

Then, a flask (heating vessel) equipped with a stirrer, thermometer, and nitrogen inlet tube was charged with 200 parts by mass of the reaction mixture, and nitrogen was introduced into the flask for 30 minutes. Thereafter, nitrogen was introduced at 10 mL/min (nitrogen feeding speed per unit volume of reaction mixture: 0.05/min), and with stirring at 250 rpm, heating was carried out under normal pressure to 200° C. The heating time was 4 hours.

Figure 2:
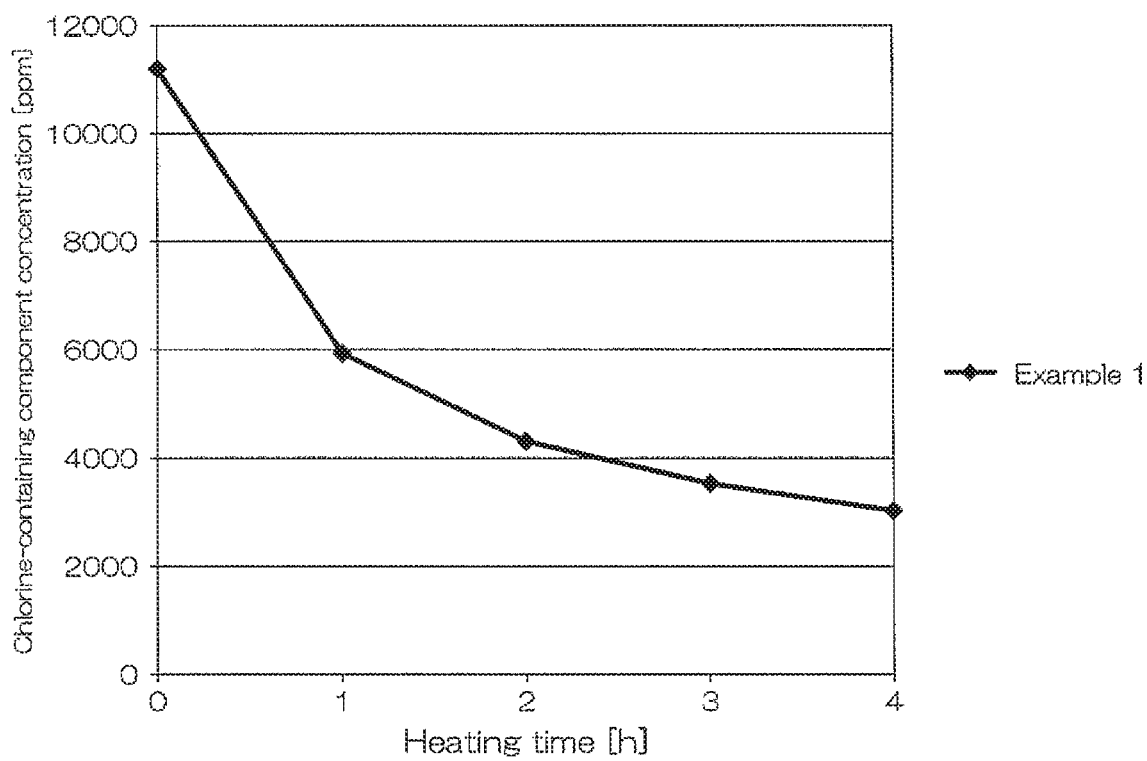
FIG. 2 is a graph illustrating the chlorine-containing component concentration relative to the heating time in Example 1.

Then, at every one hour from the start of the heating, a portion of the reaction mixture was taken as a sample, and the chlorine-containing component concentration of the reaction mixture at every hour was measured. The results are shown in Table 1 and FIG. 2.

In the above-described manner, the reaction mixture was heated without removing the tar component from the reaction mixture. Thereafter, cooling was carried out to 40° C. or less, and the reaction mixture (heated mass) after heating was obtained.

TABLE 1

| no. | Example 1 |
|---|---|
| Polyamine | PDA |
| Heating temperature[° C.] | 200 |
| Chlorine containing component concentration in reaction mixture [ppm] | |
| Heating time [h] 0 | 11195 |
| 1 | 5934 |
| 2 | 4311 |
| 3 | 3532 |
| 4 | 3028 |

<Carbonyl Chloride Generation Test>

Figure 3:
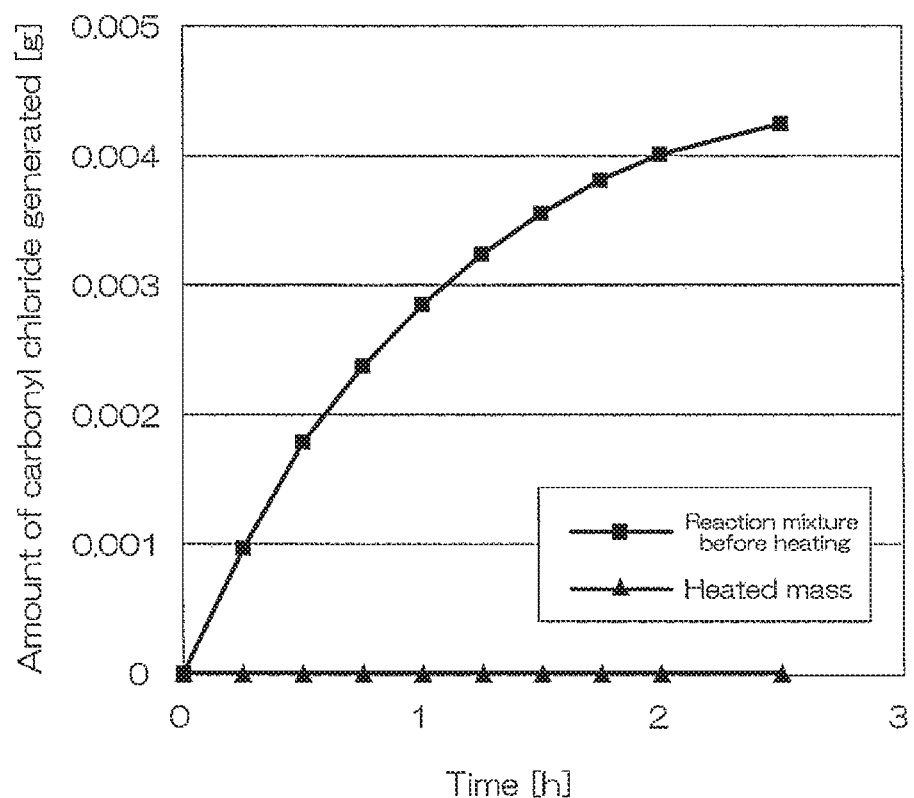
FIG. 3 is a graph illustrating the amount of carbonyl chloride generated relative to the heating time in the carbonyl chloride generation test.

A portion of the reaction mixture (reaction mixture before heating) produced in Example 1 and the heated mass (heating temperature 200° C. heating time 4 hours) was taken as a sample, and evaluated by the carbonyl chloride generation test shown below. The results are shown in FIG. 3.

A flask equipped with a stirrer, thermometer, condenser tube, and nitrogen inlet tube was charged with 200 parts by mass of the reaction mixture (reaction mixture before heating) or the heated mass, and nitrogen was introduced in the flask for 30 minutes setting the condenser tube temperature to 20° C. Then, nitrogen was introduced at 44 mL/min (nitrogen feeding speed per unit volume of reaction mixture: 0.22/min), and with stirring at 250 rpm, heating was carried out under normal pressure to 165° C. At every 15 minutes from the start of the heating, a portion (2 mL) of the discharged gas was taken as a sample with a syringe, and the carbonyl chloride content of the discharged gas at every unit of time was measured.

(3) Purification Step

Then, with a known thin film evaporator, the tar component was separated and removed from the heated mass (tar-removing step). The temperature in the thin film evaporator was 125° C., and the pressure inside the thin film evaporator was 0.13 kPa. The reaction mixture (tar-removed mass) after the tar removal, and the tar component (separated tar component) separated from the heated mass were produced in this manner.

Then, the tar-removed mass was distilled (rectified) (distillation step) with a distillation device including a stirrer, flask, and condenser tube under conditions of 120 to 150° C. and 1.7 to 2.4 kPa.

Then, after 12 mass % (12 parts by mass) of the initial fraction was distilled off, 76 mass % (76 parts by mass) the main fraction was taken as purified-pentamethylene diisocyanate. The tank bottom (distillation residue) was 12 mass % (12 parts by mass).

Comparative Examples 1 to 3

The purified-pentamethylene diisocyanate was produced in the same manner as in Example 1, except that the reaction mixture was heated after the tar removal. The results are shown in Table 2 and FIG. 4.

Comparative Examples 4 to 6

The purified-hexamethylene diisocyanate was produced in the same manner as in Comparative Examples 1 to 3, except that 1,5-pentamethylenediamine (PDA) was changed to 1,6-hexamethylenediamine (HDA). The results are shown in Table 2 and FIG. 4.

<Consideration>

As shown in FIG. 3, no carbonyl chloride was generated in the reaction mixture (heated mass) after heating in the carbonyl chloride generation test. That is, it was confirmed that in the reaction mixture (heated mass) after heating, generation of carbonyl chloride was suppressed compared with the reaction mixture before heating. Therefore, it was confirmed that in the tar component separated from the reaction mixture in Example 1, generation of carbonyl chloride was suppressed, and safety improved.

Figure 4:
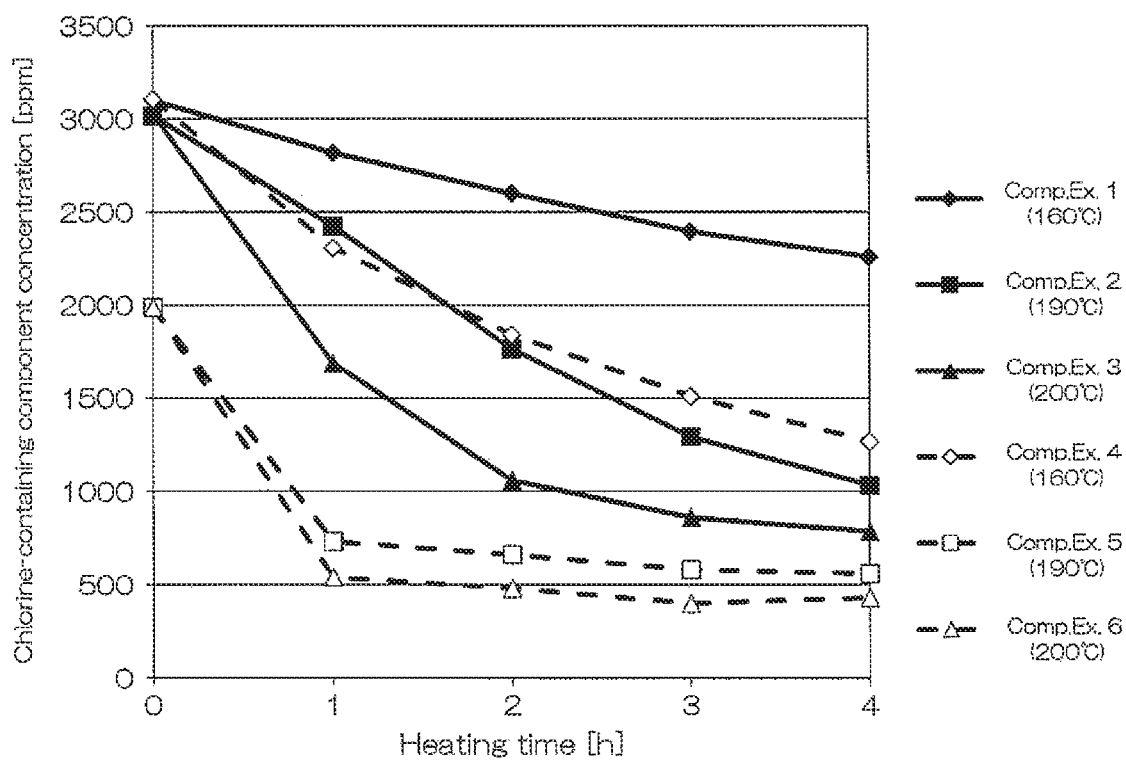
FIG. 4 is a graph illustrating the amount of carbonyl chloride generated relative to the heating time in Comparative Examples.

As shown in Table 2 and FIG. 4, it was confirmed that the reaction mixture (reaction mixture of pentamethylenediamine and carbonyl chloride) of Comparative Examples 1 to 3 contained more chlorine-containing component compared with the reaction mixture (reaction mixture of hexamethylenediamine and carbonyl chloride) of Comparative Examples 4 to 6. Also, it was confirmed that removal of the chlorine-containing component (decomposition) in the reaction mixture of Comparative Examples 1 to 3 necessitated heating with a higher temperature and/or a longer time compared with Comparative Examples 4 to 6.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The method for producing pentamethylene diisocyanate of the present invention is used suitably in various industrial fields, and pentamethylene diisocyanate produced by the method is suitably used for, for example, industrial materials in various industrials such as a polyurethane resin material.

DESCRIPTION OF REFERENCE NUMERALS

1 Plant
2 Reaction unit
5 Heating unit
6 Purifying unit

The invention claimed is:

1. A method for producing pentamethylene diisocyanate, the method comprising:
   a reaction step, in which carbonyl chloride is allowed to react with pentamethylenediamine to produce a reaction mixture containing pentamethylene diisocyanate and a tar component containing a chlorine-containing component,

TABLE 2

| no. | | Comparative Example 1 | Comparative Example 2 | Comparative Example 3 | Comparative Example 4 | Comparative Example 5 | Comparative Example 6 |
|---|---|---|---|---|---|---|---|
| Polyamine | | | PDA | | | HDA | |
| Heating temperature [° C.] | | 160 | 190 | 200 | 160 | 190 | 200 |
| | | Chlorine containing component concentration in reaction mixture [ppm] | | | | | |
| Heating time [h] | 0 | 3100 | 3018 | 3027 | 3107 | 1990 | 1990 |
| | 1 | 2818 | 2425 | 1688 | 2310 | 730 | 540 |
| | 2 | 2601 | 1766 | 1058 | 1842 | 660 | 480 |
| | 3 | 2396 | 1292 | 860 | 1510 | 580 | 400 |
| | 4 | 2260 | 1033 | 785 | 1268 | 560 | 430 | a degassing step, in which after the reaction step, excessive carbonyl chloride is removed from the reaction mixture, a heating step in which the reaction mixture after the degassing step is heated, and a purification step, in which the reaction mixture after the heating step is purified to separate the pentamethylene diisocyanate from the tar component, wherein in the heating step, the reaction mixture is heated without removing the tar component from the reaction mixture, and the purification step includes:

a tar-removing step, in which the tar component is separated from the reaction mixture, a distillation step, in which the reaction mixture after the tar-removing step is subjected to distillation to separate the pentamethylene diisocyanate from the reaction mixture, and a returning step, in which the distillation residue in the distillation step is returned to the heating step.

2. The method for producing pentamethylene diisocyanate according to claim 1, wherein the heating temperature in the heating step is more than 160° C.

3. The method for producing pentamethylene diisocyanate according to claim 1, wherein the residence time in the heating step is 1 hour or more.

* * * * *